US009084556B2

(12) United States Patent
Kakee et al.

(10) Patent No.: US 9,084,556 B2
(45) Date of Patent: Jul. 21, 2015

(54) APPARATUS FOR INDICATING LOCUS OF AN ULTRASONIC PROBE, ULTRASONIC DIAGNOSTIC APPARATUS

(75) Inventors: Akihiro Kakee, Otawara (JP);
Masahiko Yano, Otawara (JP);
Noriyuki Moriyama, Chuo-ku (JP);
Nachiko Uchiyama, Chuo-ku (JP);
Minoru Machida, Chuo-ku (JP)

(73) Assignees: Toshiba Medical Systems Corporation, Otawara-shi (JP); NATIONAL CANCER CENTER, Tokyo (JP)

( * ) Notice: Subject to any disclaimer, the term of this patent is extended or adjusted under 35 U.S.C. 154(b) by 1190 days.

(21) Appl. No.: 11/624,422

(22) Filed: Jan. 18, 2007

(65) Prior Publication Data
US 2007/0239004 A1    Oct. 11, 2007

(30) Foreign Application Priority Data

Jan. 19, 2006  (JP) ................. P2006-011447
Sep. 7, 2006   (JP) ................. P2006-242894

(51) Int. Cl.
*A61B 8/00* (2006.01)
*A61B 8/06* (2006.01)
*A61B 8/08* (2006.01)

(52) U.S. Cl.
CPC ................. *A61B 8/06* (2013.01); *A61B 8/4245* (2013.01); *A61B 8/488* (2013.01)
USPC ............... 600/443; 600/407; 600/437

(58) Field of Classification Search
USPC .......................... 600/424, 437–472; 702/150; 73/596–603, 634
See application file for complete search history.

(56) References Cited

U.S. PATENT DOCUMENTS

| 5,524,627 | A  |   | 6/1996  | Passi |
|-----------|----|---|---------|-------|
| 5,623,930 | A  | * | 4/1997  | Wright et al. ................. 600/456 |
| 5,800,352 | A  | * | 9/1998  | Ferre et al. .................... 600/407 |
| 5,868,673 | A  | * | 2/1999  | Vesely .......................... 600/407 |
| 6,063,030 | A  | * | 5/2000  | Vara et al. ..................... 600/437 |
| 6,371,913 | B2 | * | 4/2002  | Pang et al. .................... 600/441 |
| 6,449,821 | B1 | * | 9/2002  | Sudol et al. ................. 29/25.35 |
| 6,755,791 | B2 | * | 6/2004  | Kawashima .................. 600/467 |
| 2002/0087080 | A1 | * | 7/2002 | Slayton et al. ................ 600/459 |
| 2003/0078499 | A1 | * | 4/2003 | Eppstein ....................... 600/439 |
| 2004/0249291 | A1 | * | 12/2004 | Honda et al. ................. 600/476 |
| 2005/0033160 | A1 |   | 2/2005  | Yamagata et al. |
| 2005/0090746 | A1 |   | 4/2005  | Ohtake |

(Continued)

FOREIGN PATENT DOCUMENTS

JP  7-116161   5/1995
JP  2000-5178  1/2000

(Continued)

OTHER PUBLICATIONS

Office Action issued Apr. 24, 2012 in Japanese Application No. 2007-010283 (w/English translation).

*Primary Examiner* — Mark Remaly
(74) *Attorney, Agent, or Firm* — Oblon, McClelland, Maier & Neustadt, L.L.P.

(57) ABSTRACT

An apparatus and method for indicating locus of an ultrasonic probe configured to transmit and receive ultrasonic waves toward a part of a subject wherein a position or movement of the ultrasonic probe is detected, and a locus of the ultrasonic probe on an image of the part of the subject is indicated according to the detected position or movement.

16 Claims, 22 Drawing Sheets

(56) References Cited

U.S. PATENT DOCUMENTS

2005/0187463 A1* 8/2005 Quistgaard et al. .......... 600/424
2005/0256402 A1* 11/2005 Kawashima et al. ......... 600/437

FOREIGN PATENT DOCUMENTS

| | | |
|---|---|---|
| JP | 2000-512189 | 9/2000 |
| JP | 2004/121488 | 4/2004 |
| JP | 2005-118142 | 5/2005 |
| JP | 2005-169070 | 6/2005 |
| JP | 2006-400 | 1/2006 |
| JP | 2008-501436 | 1/2008 |
| WO | WO 2004/103174 A1 | 12/2004 |

* cited by examiner

APPARATUS FOR INDICATING LOCUS OF AN ULTRASONIC PROBE, ULTRASONIC DIAGNOSTIC APPARATUS

CROSS-REFERENCE TO RELATED APPLICATIONS

This application is based upon and claims the benefit of priority from the prior Japanese Patent Application No. 2006-11447, filed on Jan. 19, 2006, and Japanese Patent Application No. 2006-242894, filed on Sep. 7, 2006, the entire contents of which are incorporated herein by reference.

BACKGROUND OF THE INVENTION

An ultrasonic diagnostic apparatus displaying a body mark and a probe mark by the side of an acquired ultrasonic image is known. The probe mark is superimposed on the body mark, and indicates a position of an ultrasonic probe on a subject by showing a positional relation with the body mark. Therefore, by watching a probe mark on a body mark, an operator can identify the location of a scan plane related to an acquired ultrasonic image. Especially, in an examination of a breast or four limbs, identifying a scan plane by an ultrasonic image is very difficult. Therefore, displaying a body mark and a probe mark is very efficient for identifying a scan plane.

In a known ultrasonic diagnostic apparatus, in order to display a probe mark correctly, a three dimensional positioning system is used for detecting a position of an ultrasonic probe in real time. (For example, see JP2005-118142 and JP2005-169070.)

By the way, in a mass examination of a breast, a doctor must examine as many as possible of subjects as soon as possible. Therefore, in a recent mass examination, in order to improve examination efficiency, the examination is divided into a first examination and a second examination. The second examination is executed in the case that there is an abnormal finding and the second examination seeks to obtain a judgment as to whether the abnormal finding is benign or malignant.

Therefore, in the first examination, in order not to overlook an abnormal finding, a doctor must scan through all parts of a subject's breast. However, because a doctor concentrates on an ultrasonic image displayed on a monitor, the doctor cannot pay enough attention to operation of the ultrasonic probe, which often leads to a missed scan.

In performing the first examinations, there is a case that a doctor stores a moving ultrasonic image in accordance with continuous movement of an ultrasonic probe. Therefore, a moving image is stored while a continuous moving of an ultrasonic probe is executed. After finishing scan of all parts of the breast, many moving images are stored in a memory of the ultrasonic diagnostic apparatus.

Therefore, for an interpretation of images after examination, a doctor must search an ultrasonic image of a desirable scan plane from many moving images. In this case, the doctor refers to a body mark and a probe mark displayed as a thumbnail attached to a last ultrasonic image of a moving image.

However, because the probe mark displayed on a thumbnail is immovable, a doctor cannot identify a moving direction of an ultrasonic probe by watching the thumbnail. Therefore, in a case that ultrasonic imaging related to a desired scan plane exists in the middle of a moving image, image searching is troublesome and this leads to a decrease in examination efficiency.

BRIEF SUMMARY OF THE INVENTION

According to one aspect of the present invention, there is provided an apparatus for indicating locus of a ultrasonic probe, an ultrasonic diagnostic apparatus, a method for indicating locus of a ultrasonic probe and an ultrasonic diagnostic method in which accuracy and efficiency of the examination are improved.

According to another aspect of the present invention there is provided an apparatus for indicating locus of an ultrasonic probe configured to transmit and receive ultrasonic waves toward a part of a subject, including a detecting unit configured to detect a position or movement of the ultrasonic probe, and an locus indicating unit configured to indicate a locus of the ultrasonic probe on the part of the subject according to the position or movement detected by the detecting unit.

According to a further aspect of the present invention there is provided an ultrasonic diagnostic apparatus including an ultrasonic probe configured to transmit and receive ultrasonic waves toward a part of a subject, a detecting unit configured to detect a position or movement of the ultrasonic probe, a signal processor configured to generate an ultrasonic image related to the part of the subject on the basis of an echo signal acquired by the ultrasonic probe, and an locus indicating unit configured to indicate a locus of the ultrasonic probe on the part of the subject according to the position or movement detected by the detecting unit.

According to a further aspect of the present invention there is provided a method for indicating a locus of ultrasonic probe, including detecting a position or movement of a ultrasonic probe configured to transmit and receive ultrasonic waves toward a part of a subject, and indicating a locus of the ultrasonic probe on the part of the subject according to the detected position or movement.

According to a further aspect of the present invention there is provided an ultrasonic diagnostic method including transmitting and receiving ultrasonic waves toward a part of a subject by a probe, detecting a position or movement of the ultrasonic probe, generating an ultrasonic image related to the part of the subject on the basis of an echo signal acquired by the ultrasonic probe, and indicating a locus of the ultrasonic probe on the part of the subject according to the position or movement detected.

BRIEF DESCRIPTION OF THE SEVERAL VIEWS OF THE DRAWING

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
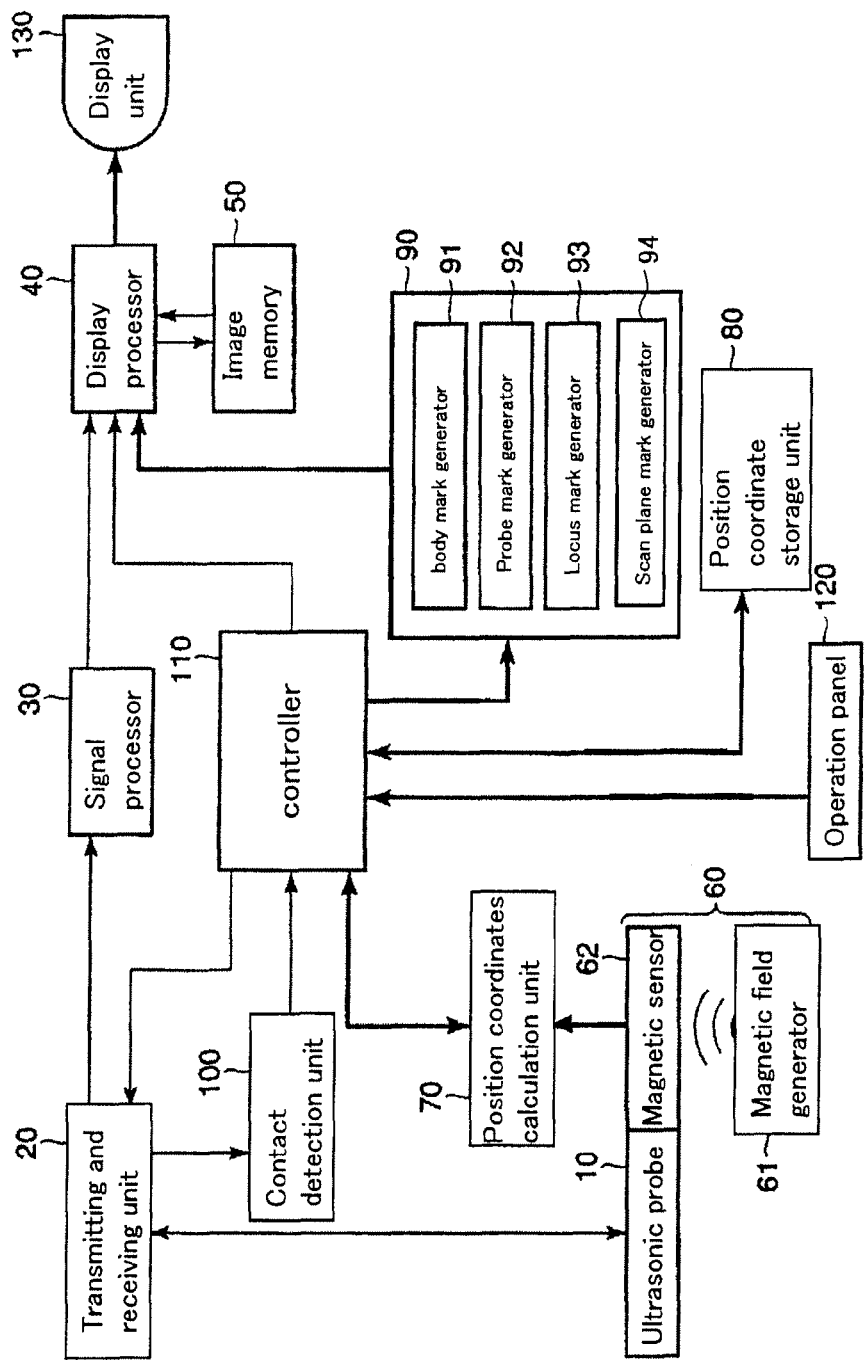
FIG. 1 is a block diagram of a first exemplary embodiment of the ultrasonic diagnostic apparatus of the invention.

Referring now to the drawings, wherein like reference numerals designate identical or corresponding parts throughout the several views, various embodiments of the present invention are next described.
(First Exemplary Embodiment)
(Components)

As shown in FIG. 1, an ultrasonic diagnostic apparatus of a first exemplary embodiment includes an ultrasonic probe 10, a transmitting and receiving unit 20, a signal processor 30, a display processor, a image memory 50, a position sensor 60, a position coordinates calculating unit 70, a position coordinates storage unit 80, a reference mark generator 90, a contact detection unit 100, a control unit 110, an operation panel 120 and a display unit 130.

The ultrasonic probe 10 transmits and receives ultrasonic to an examined part of a subject S. A piezoelectric vibrator is arranged in a casing of the ultrasonic probe 10. The piezoelectric vibrator is divided into a plurality of elements each constituting a part of a channel. If the ultrasonic probe 10 has a two dimensional arrayed vibrator, three-dimension data can be acquired.

The transmitting and receiving unit 20 includes a pulsar circuit, a delay circuit and a trigger generation circuit. The pulsar circuit repeatedly generates rate pulses for forming transmitted ultrasonic waves according to a predetermined rate frequency. The delay circuit delays each of signals through the channels for forming a focused ultrasonic beam so as to have a predetermined directivity. The trigger generation circuit transmits driving pulses to the ultrasonic probe 10 according to rate pulses generated at adjusted delay times.

The transmitting and receiving unit 20 further includes an amplifier, an A/D converter and an adder circuit. The amplifier amplifies each of echo signals through the channels obtained by ultrasonic probe. The A/D converter delays each of amplified echo signals through the channels so as to have a predetermined directivity. The adder circuit totalizes the delayed signals through a plurality of channels and generates a receiving signal. In this manner, reflected signals from predetermined directions are emphasized.

The signal processor 30 includes a B mode processing unit and a Doppler processing unit. The B mode processing unit generates a brightness data indicating intensity of a received signal by logarithmic amplifying and envelope demodulation. The Doppler processing unit calculates speed information of blood flow, tissue or contrast medium on the basis of received signals outputted by the transmitting and receiving unit 20.

The display processor 40 converts brightness data or blood flow data outputted by the signal processor 30 into video formatted data. In this way, an ultrasonic image UI is generated.

The display processor 40 also generates a reference mark RM, a body mark BM, a probe mark PM and a locus mark LM superimposed on the reference mark RM. The display processor 40 also generates a display image composed from an ultrasonic image UI and a reference mark RM related to this ultrasonic image UI.

The image memory 50 memorizes a display image generated in the display processor 40. The image memory 50 also independently memorizes a locus mark LM. In this way, an operator can see all of the locus marks memorized in the image memory 50 collectively.

The position sensor 60 utilizes a three dimension positioning system composed of a magnetic field generator 61 and a magnetic field sensor 62. The magnetic field generator 61 is set near a place, e.g., a bedside, where subject S lies. The magnetic field generator 61 generates magnetic fields having a predetermined intensity. The magnetic field sensor 62 is fixed at the ultrasonic probe and detects a magnetic field generated from the magnetic field generator 61.

The position coordinates calculating unit 70, calculates position coordinates (X, Y, Z, θX, θY, θZ) of the ultrasonic probe 10 on the basis of an intensity of a magnetic field detected by the position sensor 60 at each of predetermined times. X, Y, Z are calculated as a position of a predetermined part of a ultrasonic probe 10, and θX, θY, θZ are calculated as a gradient of an axis of a ultrasonic probe 10 to a vertical direction. Therefore a gradient of a scan plane of an ultrasonic probe 10 can be calculated from θX, θY, and θZ.

The position coordinates storage unit 80, stores time lengths that indicates how long a ultrasonic probe 10 touches subject S continuously and position coordinates of a ultrasonic probe 10 at each of plural time intervals. In this way, coordinates data indicating moving of an ultrasonic probe 10 are stored in the position coordinates storage unit 80.

The reference mark generator 90 includes a body mark generator 91, a probe mark generator 92, a locus mark generator 93 and a scan plane mark generator 94.

The body mark generator 91 generates a body mark BM according to a part to be examined on the basis of information of a subject S that is preliminarily inputted by means of the operation panel 120. In this exemplary embodiment, a part to be examined is a breast. A body mark is generated in a likeness of a breast. The body mark BM may be selected from a menu of body marks each indicating a different part of the body.

The probe mark generator 92 generates a probe mark PM which indicates a position of a surface of a piezoelectric vibrator of the ultrasonic probe 10 on the basis of position coordinates of the ultrasonic probe 10 detected by the position sensor 60.

The locus mark generator 93 generates a locus mark LM, which indicates a locus of the ultrasonic probe 10 on the basis of a coordinates data, stored in the position coordinates storage unit 80.

The scan plane mark generator 94 generates a scan plane mark SM that indicates a region where the ultrasonic probe 10 is presently imaging.

The contact detection unit 100 detects a contact between an ultrasonic probe 10 and a subject S on the basis of an echo signal from the transmitting and receiving unit 20.

The controller 110 includes a CPU that is driven by software, and controls every part of the ultrasonic diagnostic apparatus. The controller 110 also makes the locus mark generator 93 and the scan plane mark generator 94 generate a locus mark LM and a scan plane mark SM on the basis of a detection result of the contact detection unit 100.

The operation panel 120 includes an input switch for inputting information related to the subject S, which is, for example, an ID of the subject S or a part to be examined. The operation panel 120 also includes a position determination switch for determination of position coordinates of the ultrasonic probe 10 during calibration, discussed below, and a locus display switch for displaying all locus marks stored in the position coordinates storage unit 80.

Figure 3:
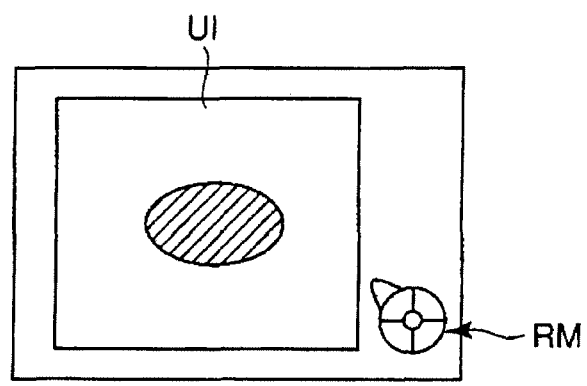
FIG. 3 is an abstract chart of a displayed image of the first exemplary embodiment.

The display unit 130 displays, as shown in FIG. 3, a display image including the ultrasonic image UI and a reference mark generated by the display processor 40. The display unit 130 also displays on demand all locus marks stored in the position coordinates storage unit 80 upon operation of the locus display switch of the operation panel 120.

In the above explanation, all components are constructed in an ultrasonic diagnostic apparatus. However, the noted components may be constructed as an external unit or in terms of one or more software components. For example, the position sensor 60, the position coordinates calculating unit 70, the position coordinates storage unit 80 and the reference mark generator 90 may be constructed as an external unit that can be added to a conventional ultrasonic diagnostic apparatus. Furthermore, the position coordinates calculating unit 70, the position coordinates storage unit 80 and the reference mark generator 90 may be implemented in software processed by the CPU of the controller 110.

(Operation)

Figure 2:
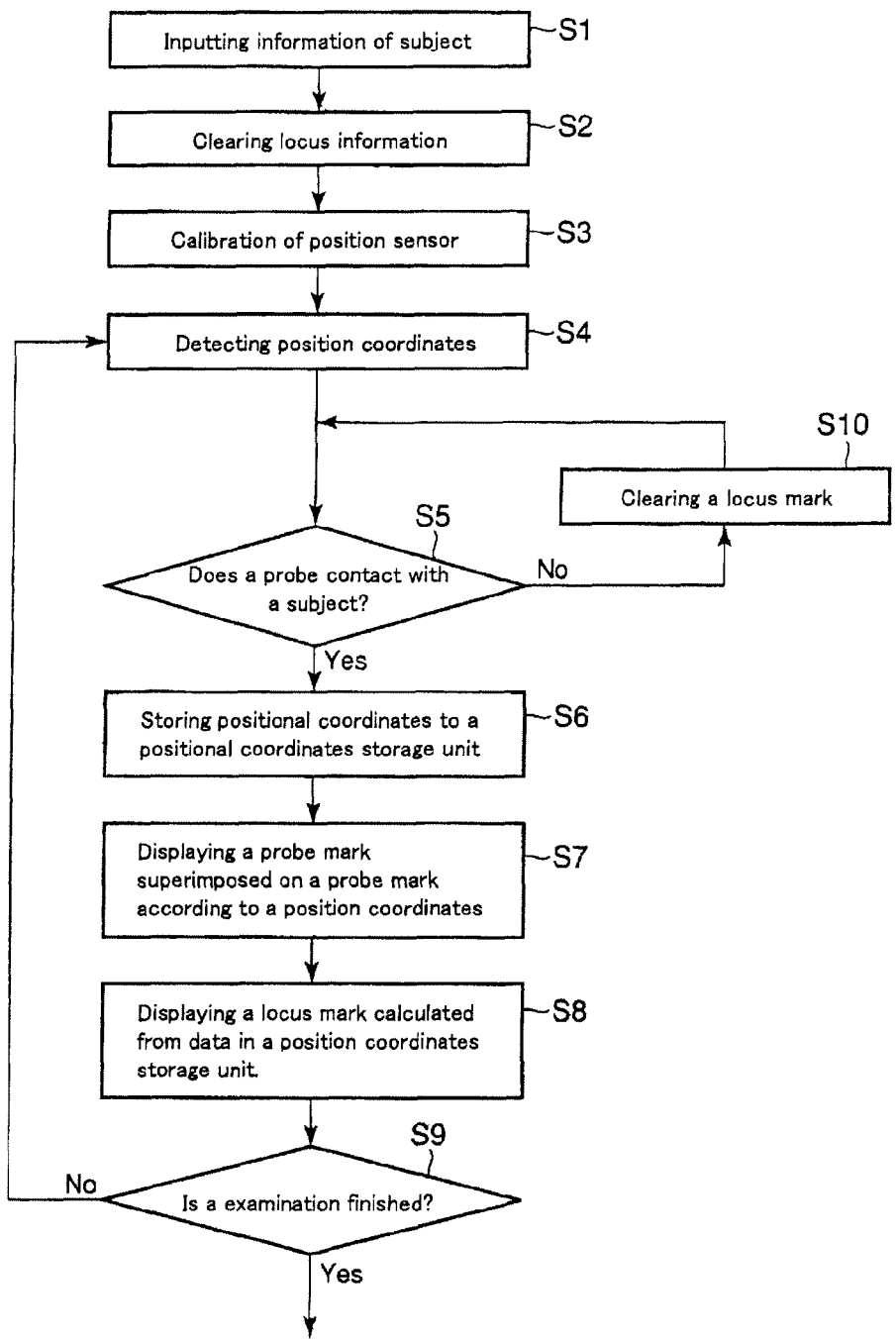
FIG. 2 is a flow chart of an examination process by the ultrasonic diagnostic apparatus of the first exemplary embodiment.

Next, a process of examination of the first exemplary embodiment is explained in reference to FIG. 2.

At first, various information, for example, an ID of a subject S or a part to be examined is inputted. (Step S1) At the next step, the body mark generation unit 91 generates a body mark BM according to the part to be examined. In this exemplary embodiment, because the part to be examined is a breast, a body mark BM resembling a real breast is generated. The body mark BM is sent to the display processor 40 and combined with an ultrasonic image UI generated by ultrasonic scans.

Next, positioning coordinates data of position of the ultrasonic probe 10 that is remained in the position coordinate storage unit 80 and stored before that time is cleared. (Step S2) In the case that no examination has been carried out, no data is cleared.

Figure 4:
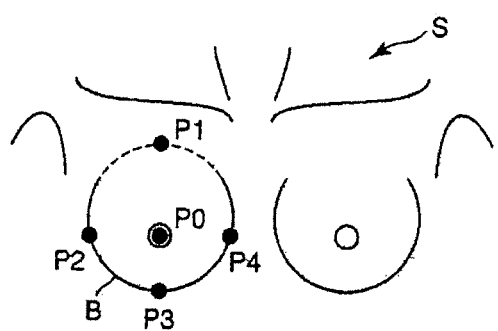
FIGS. 4(a) and 4(b) are abstract charts for an explanation of calibration of a position sensor of the first exemplary embodiment.
Figure 4:
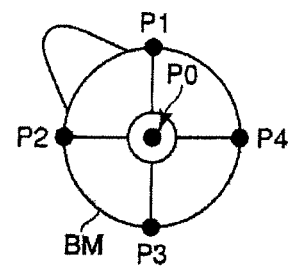

Next, calibration of the positioning sensor 60 is executed. (Step S3) In this calibration, as shown in FIG. 4(*a*), an ultrasonic probe 10 touches five predetermined points of a breast B (P0-P4). The position fixing is executed by an operation of the operation panel 120 when the ultrasonic probe 10 touches the predetermined points. By this means, position coordinates (X, Y, Z) of the points P0-P4 of breast B is related to points P0-P4 predetermined on a body mark BM. In this exemplary embodiment, calibration of relative relationship of positions between a body mark B and a breast B of the subject S and calibration of relative relationship of positions between the ultrasonic probe 10 and a breast B of the subject S are carried out in a common step.

Each of position information of the parts P0-P4 is three-dimensional position information. Several methods are supposed for relating such three-dimensional position information to a two-dimensional body mark. For example, by ignoring the coordinate of the perspective direction, the three-dimensional information may be related to the two-dimensional body mark. Also, two-dimensional information may be acquired by projecting the P0-P4 to a plane that is fitted to the coordinates of P0-P4. Furthermore, the body mark BM may be related as a spread form of a breast that indicates a superficial area of a breast.

If calibration is not so accurate, a relation between an ultrasonic image UI and reference mark RM becomes incorrect. Therefore, it is desirable for an operator to fit the ultrasonic probe 10 to the positions P0-P4 accurately. It may be predetermined how to fit the ultrasonic probe 10 to the points. For example, the ultrasonic probe 10 may be fit by reference to a predetermined part of the ultrasonic probe. The predetermined part may be a center pointer an end point of the surface of the piezoelectric violator. The ultrasonic probe may have a mark that is arrow shape, triangle shape, line or dot for indicating the predetermined part. An operator may position the ultrasonic probe so that the predetermined part lies on the position of P0-P4. The position sensor 60 has information relating where the predetermined point positions are at a view of the ultrasonic probe 10. Such information indicates the position of the predetermined point in the ultrasonic probe, whereby the position sensor can detect the correct positional relationship between the subject and the ultrasonic probe. After the above discussed calibration process of the position sensor 60, the position sensor 60 detects position coordinates of the ultrasonic probe 10 (step S4). In addition, the position sensor 60 carries on detecting of position coordinates of the ultrasonic probe 10 until completion of all processes of an examination.

Figure 5:
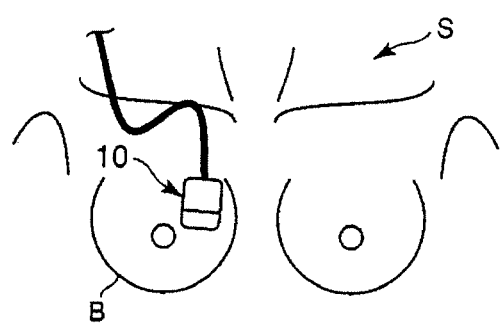
FIG. 5 is an abstract chart of an ultrasonic probe on a subject of the first exemplary embodiment.

After detection of position coordinates of ultrasonic probe 10, as shown in FIG. 5, an operator brings the ultrasonic probe 10 into contact with a breast B of subject S and moves the ultrasonic probe 1.0 along an axis of a body of the subject S. An operator may move the ultrasonic probe 10 along a virtual circle centered around a nipple of the breast of the subject S.

After detecting of contact of the ultrasonic probe 10 with subject S (an YES route of the step S5), the position coordinates calculation unit 70 calculates position coordinates of the ultrasonic probe 10 at each of predetermined times. The position coordinates are stored in the position coordinates storage unit 80 (step S6). In this manner, the position coordinates storage unit 80 stores the coordinates data consisting of time data of elapsed times from contacting of the ultrasonic probe 10 with the subject S and position coordinates data related to each of the elapse times.

Figure 6:
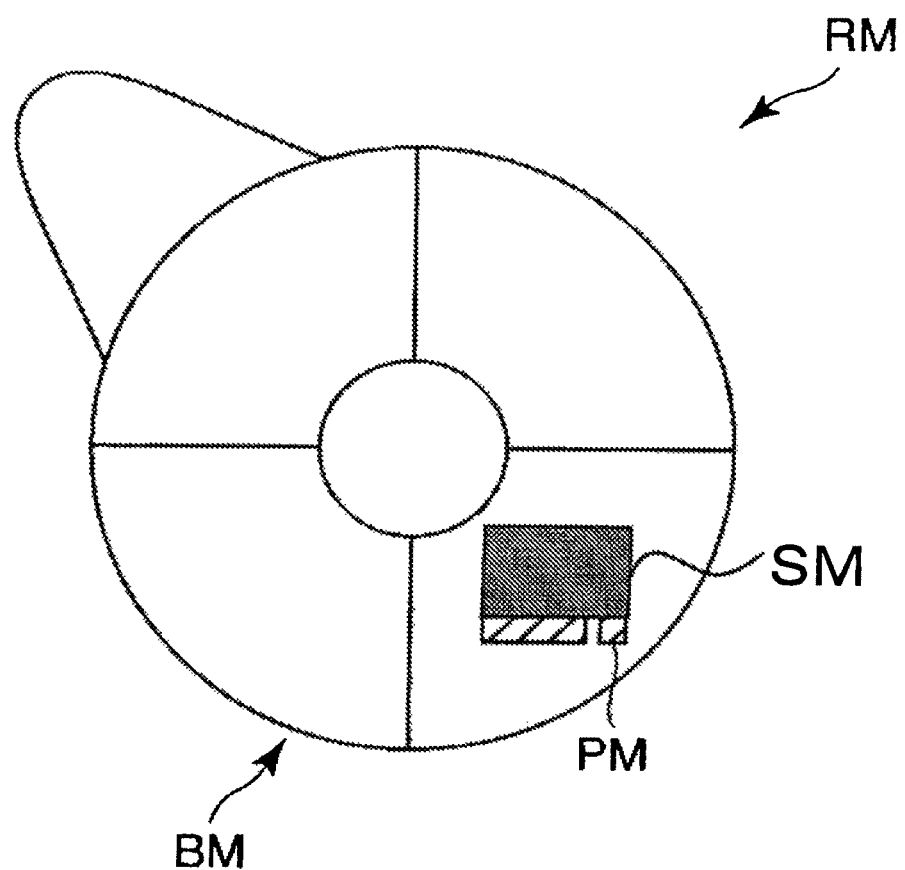
FIG. 6 is an abstract chart of a reference mark superimposed with a scan plane mark of the first exemplary embodiment.

Next, the probe mark generator 92 generates a probe mark PM on the basis of the coordinates data stored in the position coordinates storage unit 80. The probe mark PM is sent to the display processor 40 and superimposed on the body mark BM already generated and displayed on the display unit 130 as shown in FIG. 6 (step S7). In this exemplary embodiment, the probe mark PM has a notch near its end as shown in FIG. 6. The notch is for indicating which end of the ultrasonic probe 10 related to the notched end of the probe mark PM. The ultrasonic prove 10 or ultrasonic image UI may have a mark related the notch. An operator can understand the relationship of direction between the ultrasonic image UI and probe mark PM. Furthermore such a mark of the probe mark PM is not limited to the notch; it may be circle, dot, or arrow shape near/on the probe mark PM.

At the same time, the locus mark generator 93 generates a locus mark on the basis of the coordinates data stored in the position coordinates storage unit 80. In the position coordinates storage unit 80, position coordinates of the ultrasonic probe after contacting of the ultrasonic probe 10 with the subject S until present time are memorized. Therefore, on the basis of continuous position coordinates of the ultrasonic probe 10, the locus mark LM indicates how the ultrasonic probe 10 has moved on the subject S. In concrete terms, based on each position coordinate, each of coordinates of positions of ends of a contacting surface of the ultrasonic probe 10 is calculated and the locus mark LM is made by marking at coordinates of positions of ends.

The scan plane mark generator 94 generates a scan plane mark SM. The scan plane mark SM is generated as a mark indicating, as shown in FIG. 6, a form of a scan plane of ultrasonic signal that is transmitted from the ultrasonic probe 10 and is projected from upside of the breast B. In this manner, an operator can see to what degree the scan plane extends along a direction of a body surface.

For example, the degree of the scan plane may be indicated on the basis of a degree to a vertical. For another example, the degree may be indicated on the basis of the position of P0-P4. In this case, the scanned surface of the object is approximated by a plane fitted by the position of P0-P4.

Because the position coordinates (X, Y, Z, θX, θY, θZ) of the ultrasonic probe 10 are generated by the position sensor 60 and the position coordinates calculating unit 70, on the basis of the θX, θY, θZ indicating the degree to vertical direction, the degree of the ultrasonic probe 10 to the approximated surface of the object is calculated.

Furthermore, on the basis of the degree of the ultrasonic probe 10 and a set transmitting and receiving condition, a real scan plane position, which indicates an imaged region, is once generated as a three dimensional information. Then two dimensional projection information of the three dimensional information of the scan plane is generated by projection from perpendicular to the approximated surface. The two-dimensional projection information is superimposed on the body mark BM as the scan plane mark.

The scan plane mark generator 94 also acquires information related to a region to be scanned from the control unit 110, and reflects the information to a form of the scan plane mark SM. For example, an operator can adjust depth of image by operating the operation panel 120. When an operator increases depth, a interval of transmitting ultrasonic pulse became longer, the imaged region of ultrasonic image UI is deeper and one can see deeper part of the object. This parameter of depth indicates how long ultrasonic images UI along a longitudinal direction. When depth is changed, the real scan region changes, so scan plan mark is deservingly changed according to depth.

Figure 7:
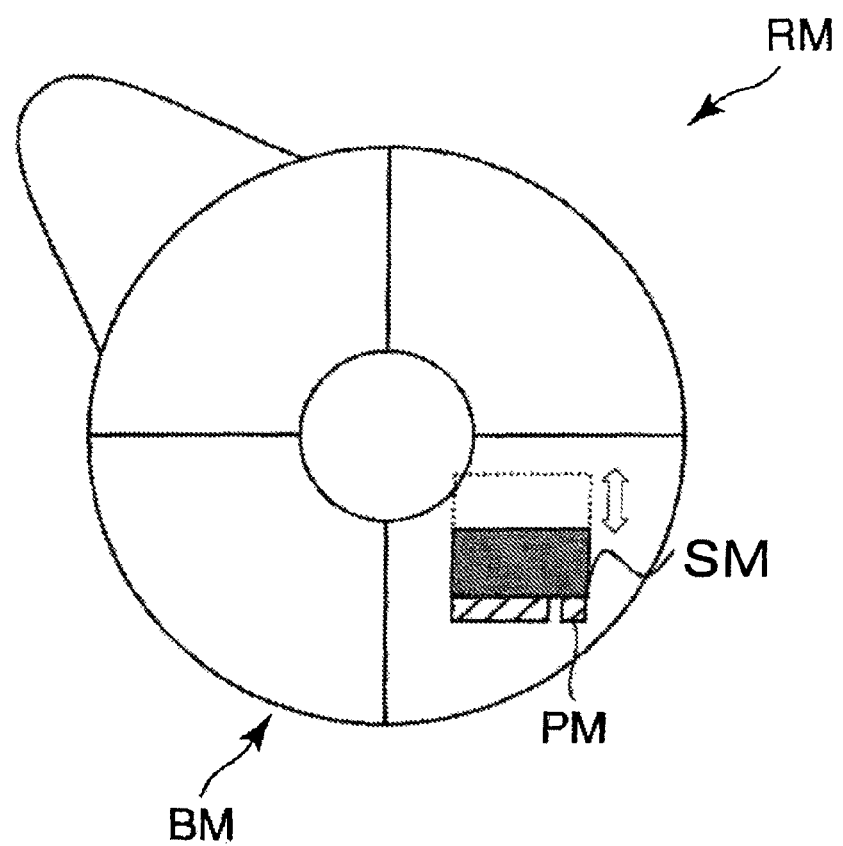
FIG. 7 is an abstract chart of a reference mark when a depth of imaged region is changed in the first exemplary embodiment.

As shown in FIG. 7, the scan plane mark SM is transformed according to depth information. If a shaded area of FIG. 7 is displayed as the scan plane mark at first, in accordance with increase of depth, scan plane mark SM is transfer like an unshaded area of FIG. 7. In this case, the angle of the ultrasonic probe 10 is fixed and not perpendicular to surface of the object. When the ultrasonic probe 10 is fixed in perpendicular to surface of the object, scan plane mark SM hardly displayed at any depth level.

Figure 8:
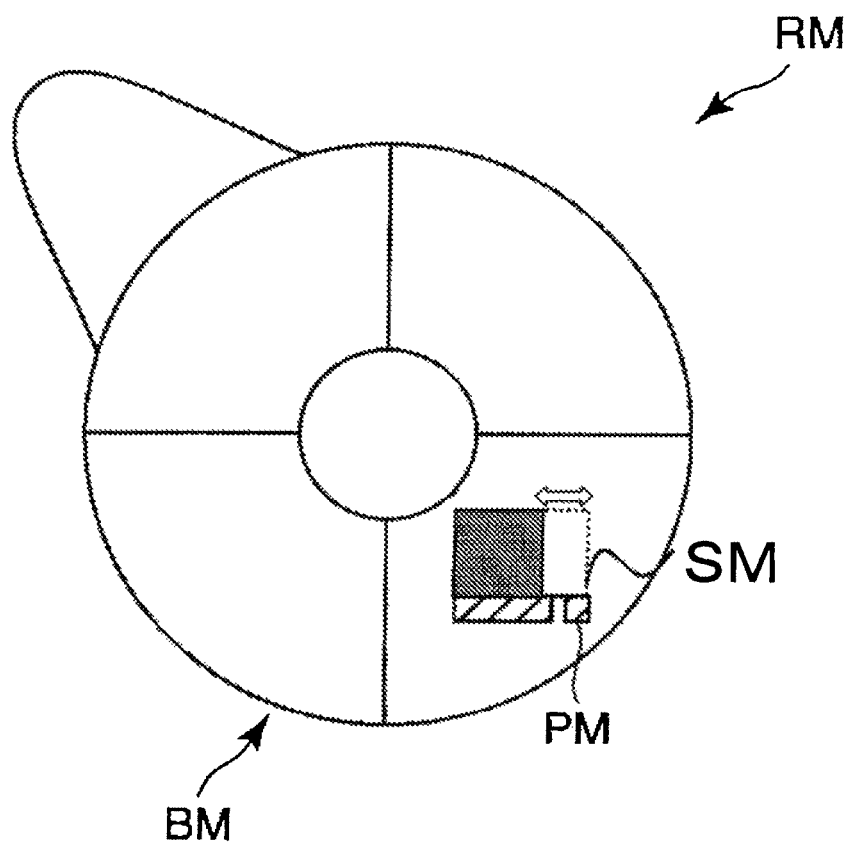
FIG. 8 is an abstract chart of the reference mark when an aperture of imaged region is changed in the first exemplary embodiment.

An operator also can adjust horizontal range of the form of the scan plane mark SM. In this case, as shown in FIG. 8, the form of the scan plane mark SM is transformed according to a change of the aperture of a scanning range.

Figure 9:
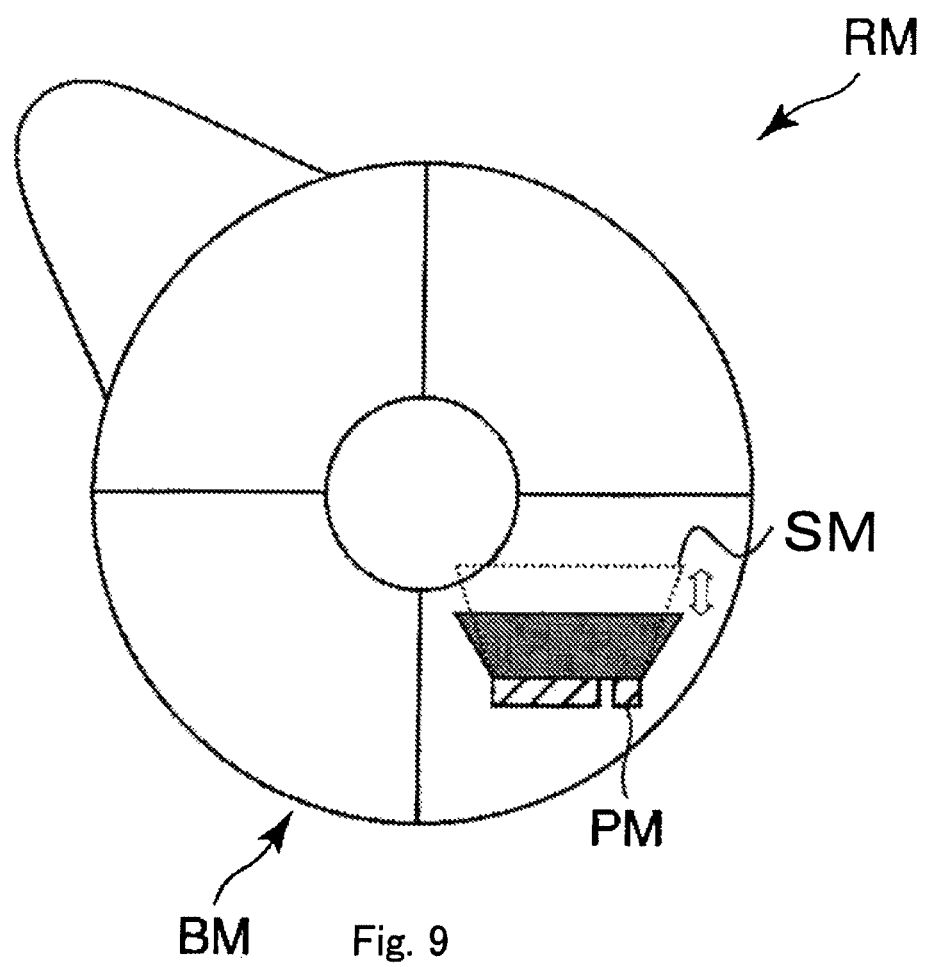
FIG. 9 is an abstract chart of the reference mark when a trapezoid region is scanned in the first exemplary embodiment.
Figure 10:
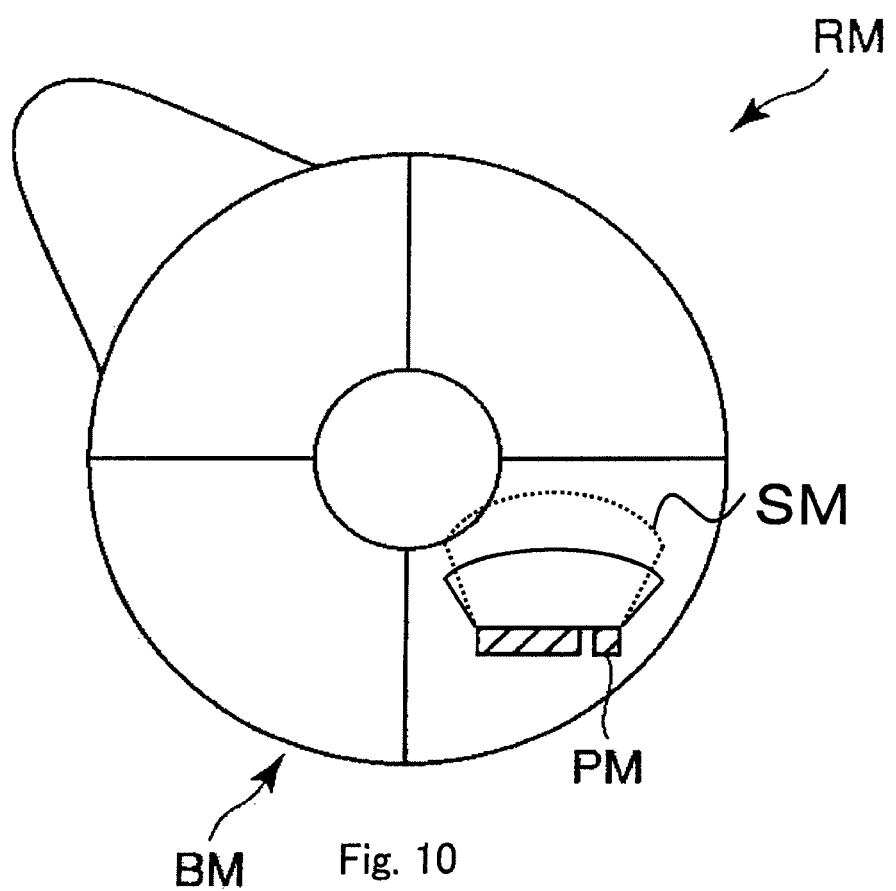
FIG. 10 is an abstract chart of the reference mark when a convex probe or sector probe is used in the first exemplary embodiment.

A scan region may be different according to the kind of ultrasonic probe 10. To accommodate such different scan regions the form of the scan plane mark SM is corresponding transformed to match the scan region of the probe employed. For example, when a trapezoid scan is executed, the scan plane mark SM is displayed as shown in FIG. 9. In the case of usage of a sector or convex type probe, the scan plane mark SM is formed in a funnel like form as shown in FIG. 10. In addition, it is needless to say that the form of probe mark PM also could be transformed according to a form of the ultrasonic probe 10.

Figure 11:
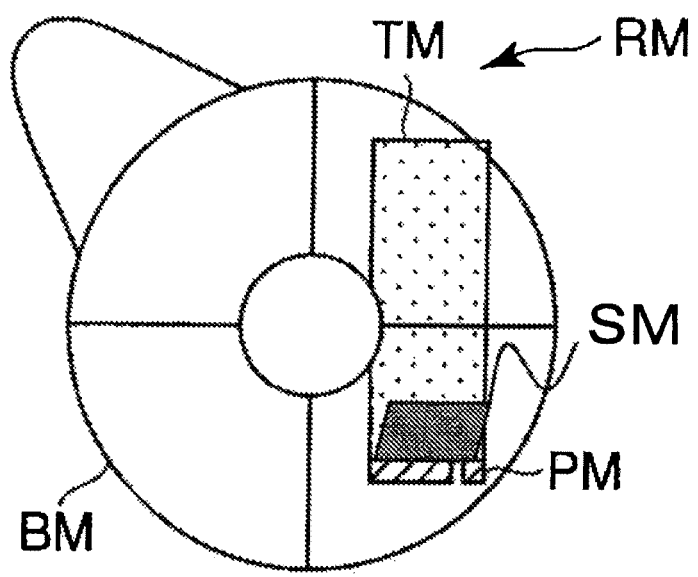
FIG. 11 is an abstract chart of the reference mark when an ultrasonic probe is moved along an axis of the subject body in the first exemplary embodiment.
Figure 12:
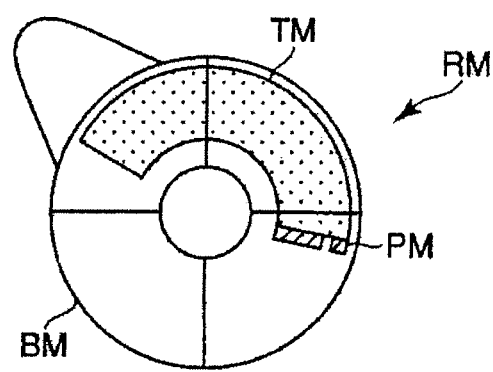
FIG. 12 is an abstract chart of the reference mark when an ultrasonic probe is moved along a virtual circle centered around a nipple of the subject in the first exemplary embodiment.

These locus mark LM and scan plane mark SM are sent to the display processor 40 and superimposed on the body mark BM already generated and displayed on the display unit 130 as shown in FIG. 11 (step S8). In addition, in the case the ultrasonic probe 10 moves along a virtual circle centered around a nipple of the breast of the subject S, as shown in FIG. 12, the locus mark LM becomes a ring form.

It is desirable that when the probe mark PM, the locus mark LM and the scan plane mark SM are generated, the probe mark generator 92, the locus mark generator 93 and the scan plane mark generator 94 convert a relative position and a relative angle of the ultrasonic probe 10 to the breast B into a relative position and a relative angle of the probe mark PM, the locus mark LM and scan plane mark SM to the body mark BM. In this manner, by only seeing the probe mark PM, the locus mark LM and the scan plane mark SM superimposed on the probe mark PM, an operator can confirm a position and a locus of an ultrasonic probe and imaged scan region.

As shown in FIG. 3, the ultrasonic image UI and the related reference mark RM are displayed side by side by the display unit 130. Therefore, an operator can confirm which portion of the subject is related to ultrasonic image UI.

After the ultrasonic probe 10 has moved some distance, the ultrasonic probe 10 may be separated from the surface of subject S once. An operator then contacts the ultrasonic probe 10 with the breast B of the subject S once again, and moves the ultrasonic probe 10 along the surface of the breast B. At this time, the ultrasonic probe 10 is displaced so as not to scan regions already scanned.

Figure 13:
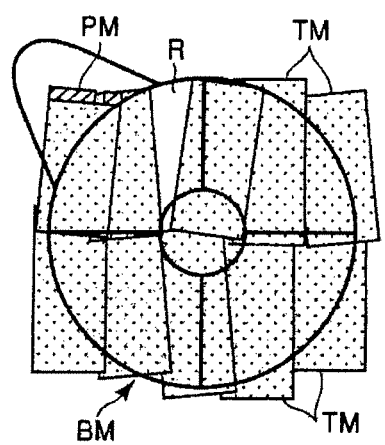
FIG. 13 is an abstract chart of the reference mark when all of the locus marks are displayed of the subject in the first exemplary embodiment.

After a several times of such operations of the ultrasonic probe, by pushing the locus display switch on the operation panel 120, an operator can order display of all of the locus marks LM that have been generated before that time, as shown in FIG. 13.

When an operator finds a region R of the body mark BM that is not covered by the locus marks LM, the operator can recognize that the region R has not yet been scanned and then scans the region R by the ultrasonic probe 10 (a no route of step S9). Finally, when all parts of the body mark BM are covered by the locus mark LM, an operator can recognize that scan of the breast B of the subject S is finished ("yes" route of step S9).

In addition, when the ultrasonic probe 10 is separated from the subject, contact detection unit 100 detects the separation, whereupon the locus mark LM and scan plane mark SM are displayed until such time they are cleared (step S10). In this manner, only while the ultrasonic probe 10 contacts the subject S, the locus mark LM and the scan plane mark SM superimposed on body mark are displayed.

(Search of Images)

Next, for example after first examination, the process of searching a particular ultrasonic image UI from a plurality of moving images is explained.

For example, after first examination there is the case that a plurality of ultrasonic images UI is stored as a moving image. In this case, a doctor identifies a moving image including an abnormal finding by reference to the reference marks RM related to the last ultrasonic image of each moving image listed up as thumbnails. At the next step, by reviewing the scan plane mark SM and the locus mark LM of the reference mark and the moving images, a doctor operates the display unit 130 to display a particular ultrasonic image UI which includes an abnormality.

(Superimposing a Lattice Pattern)

Figure 14:
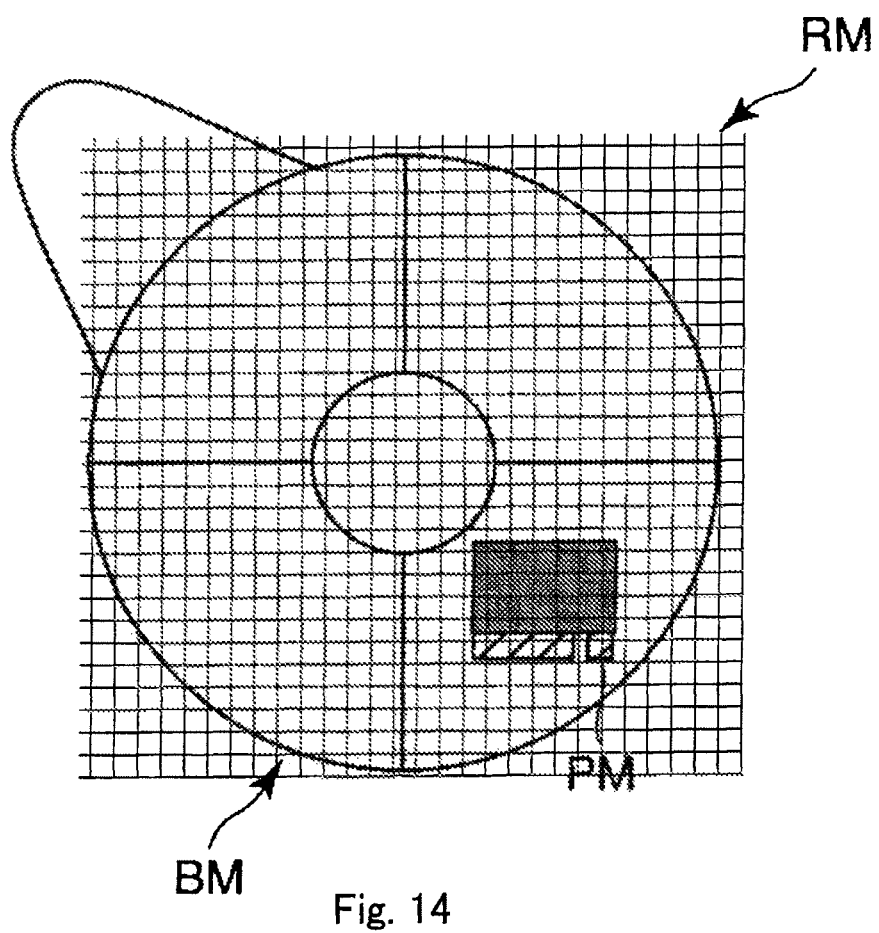
FIG. 14 is an abstract chart of the reference mark when a lattice pattern is displayed in the first exemplary embodiment.

In addition, in order to simplify understanding of positional relationships, as shown in FIG. 14, a lattice pattern uniformly spaced may be superimposed on the body mark BM. Furthermore, a scaled axis or uniformly spaced dots patterns can be used as an alternative to the lattice pattern.

Furthermore, on the basis of the calibration result of the position sensor 60, the spaces the lattice pattern may be determined. This results in the lattice reflecting actual sizing, whereby it becomes easier to recognize real distances on the breast B by watching the reference mark RM. Displaying a scale lattice spacing corresponding to actual distances may also have the same effect.

(Effect)

In this exemplary embodiment, each locus from a start of an examination of a breast is displayed as the locus mark LM on the body mark BM. Therefore, merely by viewing the body marks and the locus mark LM, an operator can recognize non-scanned areas of the breast B. As a result, a complete ultrasonic scan over the entire breast B can be obtained in reduced time, and accuracy and efficiency of the examination are improved.

In this exemplary embodiment, the present scan plane of the ultrasonic probe images is displayed as the scan plane mark SM on the body mark BM. Therefore, only by viewing the body mark and the scan plane mark SM, an operator can recognize an imaged scan area at a particular time, whereby the actual position of the displayed ultrasonic image UI is easily recognized. Furthermore, for a same time viewing of the scan plane mark SM and the locus mark LM, an operator can recognize the scanned area of the breast B more surely and a complete ultrasonic scan of the entire breast B can be executed, whereby accuracy and efficiency of the examination are improved.

In this exemplary embodiment, only when a locus display switch on the operation panel 120 is pushed, the locus mark LM is displayed on the body mark BM. Therefore, because only one locus mark LM is displayed on the body mark BM while scanning of the breast B, display visibility to the operator is good.

In this exemplary embodiment, only when the ultrasonic probe 10 is contacted with the subject S, are the probe mark PM, the scan plane mark SM and the locus mark LM displayed. This results in good display visibility to the operator.

In this exemplary embodiment, when the ultrasonic image UI stored as moving image is reviewed, reference mark RM is displayed by the ultrasonic image UI. Therefore, even in the case of reviewing after first examination, only by watching the reference mark RM, the operator can easily identify a scan plane including an abnormality.

Second Exemplary Embodiment

Figure 15:
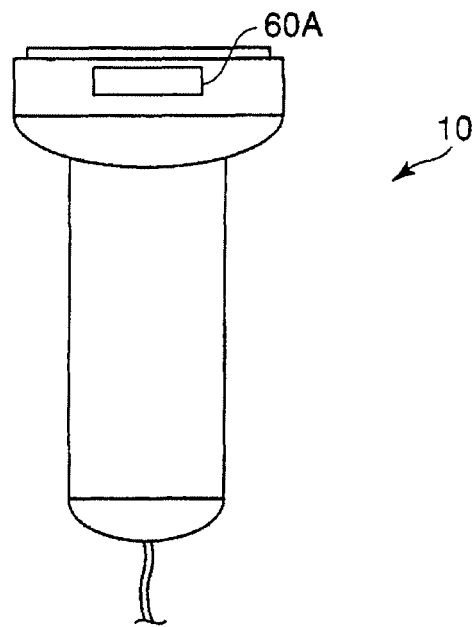
FIG. 15 is an abstract chart of an ultrasonic probe of a second exemplary embodiment.

Next, a second exemplary embodiment is explained with reference to FIG. 15 and FIG. 16.

In the first exemplary embodiment, a three-dimensional positioning system is used as the position sensor 60 for detecting position coordinates of ultrasonic probe 10. However, in the second exemplary embodiment, as shown in FIG. 15, an image sensor, e.g., often used in an optical mouse, is used as a position sensor 60A.

The position sensor 60A is fixed at the ultrasonic probe and detects distance and direction of moving of the ultrasonic probe 10. Therefore, the position sensor 60A cannot detect absolute position coordinates of the ultrasonic probe 10 in the same way as the position sensor 60 in the first exemplary embodiment. However, the image sensor in the position sensor 60A is less expensive than the magnetic sensor 62. Furthermore, usage of the image sensor 60A is uninfluenced by a disturbance of magnetic field due to metals or such materials so use of the sensor 60A is not limited by location.

Figure 16:
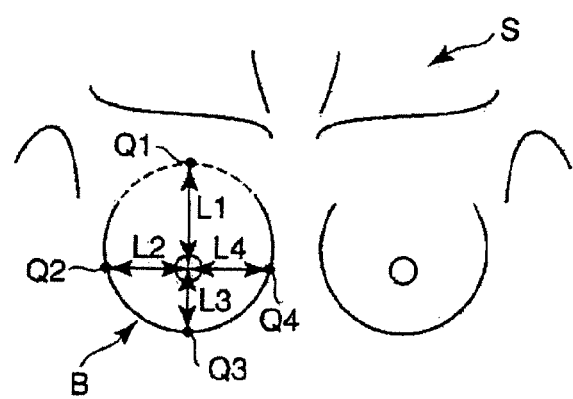
FIGS. 16(a) and 16(b) are abstract charts for explanation of calibration of the position sensor of the second exemplary embodiment.
Figure 16:
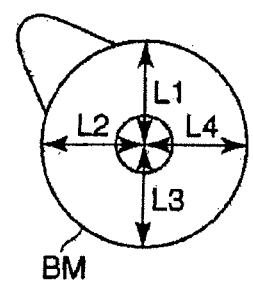

As shown in FIG. 16, in calibration of the position sensor 60A of this exemplary embodiment, at first an operator contacts the ultrasonic probe 10 with the nipple of the breast B. At a next step, as shown in FIG. 16(*a*), the operator moves the ultrasonic probe 10 toward parts Q1-Q4. In this manner, distances L1-L4 from the nipple toward the four parts arranged around the breast B are measured. The distances L1-L4 are related to distances L1-L4 on the body mark BM. Thus, in the calibration of this exemplary embodiment, only a relative relationship between the body mark BM and the breast B is calibrated. A relative relationship between the ultrasonic probe 10 and the breast B is not calibrated.

After the above noted calibration, an operator maintains contact of the ultrasonic probe 10 with the breast B, and at same time, moves the ultrasonic probe 10 in each direction. If the ultrasonic probe 10 separates from a surface of the breast B, when the ultrasonic probe is re-contacted with the breast B, the operator moves the body mark BM to a position related to the position where the ultrasonic probe 10 touches the breast by operating the operation panel 120. In this manner, the relative relationship between the body mark BM and the breast B is reestablished, which is desirable in this exemplary embodiment because a relative relationship between the ultrasonic probe 10 and the breast B is not calibrated.

(Third Exemplary Embodiment)

Figures 16, 17:
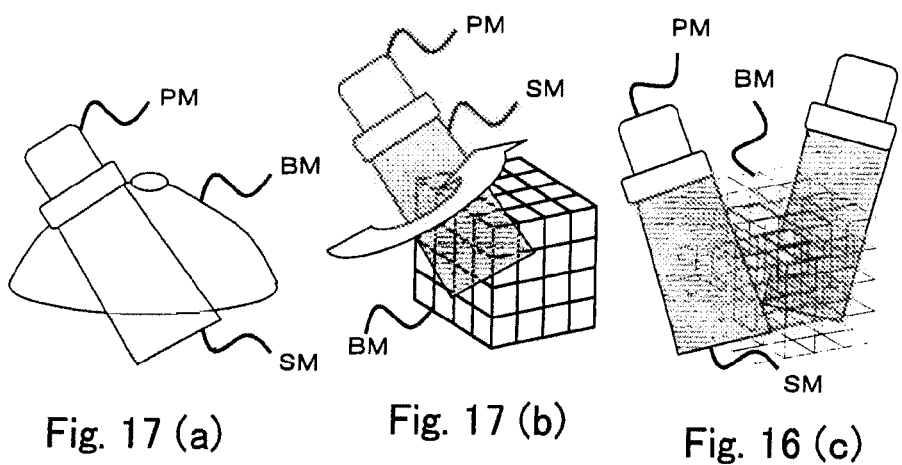
FIGS. 17(a), 17(b) and 17(c) are abstract charts of the reference mark of the third exemplary embodiment.

Next, a third exemplary embodiment is explained with reference to FIG. 17.

In the second exemplary embodiment, the body mark BM is displayed in a two dimensional form. However, in this exemplary embodiment, a body mark BM and a locus mark LM are displayed in a three dimensional form.

At first, generation of the body mark BM will be explained. At a first step, position coordinates (X, Y, Z) of every part of P0-P4 of the breast B are obtained. These coordinates indicate three dimensional position information, so on the basis of this position information, a three dimensional form of the breast B is calculated. The probe mark generator 91 generates a body mark which indicates a three dimensional view of the breast B. One example of such a body mark of the breast B in perspective view is shown in FIG. 17(*a*). The body mark BM may be in wire frame form or in the form of a plurality of cubic blocks. In this exemplary embodiment, the probe mark BM is formed by a plurality of cubic blocks.

Next, generation of a probe mark PM and a scan plane mark SM are explained. On the basis of the generated positional relation, a probe mark PM and a scan plane mark SM are displayed so that the positional relation of the ultrasonic probe and a scan plane is understandable on the basis of the generated positional relation. In FIG. 17, the form of the probe mark PM indicates a whole form of ultrasonic probe. But, it may be in a simple form composed of lines or squares only indicating the ultrasonic emitting surface. Next, display of locus is explained. In FIGS. 17(b) and 17(c), the body mark BM has a cube form as a matter of convenience of explanation. However, a practical body mark is provided in the form of multiple cubic blocks arranged so as to have a form similar to the form of the breast. The locus mark generator, on the basis of position information and transmitting and receiving condition, erases cubic blocks related to a region already imaged. Thus, at the beginning of an examination, the probe mark PM is as shown in FIG. 17(b), and the probe mark PM is cut by the moving of the ultrasonic probe 10 as shown in FIG. 17(c), and the completion of imaging, the probe mark PM finally disappears. The disappearance of the probe mark PM means that the entire three dimensional region of the breast B has been scanned. Therefore, an operator tries to move the ultrasonic probe so as to erase all of the probe mark PM. In this case, the locus mark is evidenced by erasure of the entire probe mark. In addition, a color of the cubic block composing the probe mark PM may be changed. In this case, the color block related to a region already scanned may become half transparent or a cubic frame having transparent planes so as to make inside cubic blocks visible.

In this exemplary embodiment, because the probe mark PM and the body mark BM is displayed in a three dimensional manner, a three dimensional understanding of the scanned region becomes easy. Accordingly, accuracy and efficiency of examination are improved.

Furthermore, in this exemplary embodiment, because a part of the body mark BM related to the already scanned body part is erased in a three dimensional manner, it is clear whether there is a region not yet scanned. Therefore, instances of unscanned regions are reduced and it becomes easy to acquire an ultrasonic image of the whole region of a breast. Once again, accuracy and efficiency of the examination are improved.

(Fourth Exemplary Embodiment)

In a fourth exemplary embodiment, positions of abnormalities such as a tumor or lesion are memorized.

After finding an abnormality, an operator places the center of the abnormality on an ultrasonic image. Next, the controller 110 determines the positional information (Xi, Yi) of the abnormality on the image. The controller 110 also acquires positional coordinates (X, Y, Z, θX, BY, θZ) of the ultrasonic probe 10 at the time of acquisition of the ultrasonic image including the abnormality. On the basis of such information, the controller 110 determines and memorizes positional information of the abnormality.

Several formats may be used for memorized positional information of the abnormality. At first, absolute coordinates of the abnormality are acquired from (Xi, Yi), (X, Y, Z, θX, θY, θZ). The absolute coordinates in this case are defined in a coordinates system based on the subject or preferably a coordinates system having an origin at a nipple. In this manner, it is possible to mark a part related to the abnormality on each ultrasonic image. In addition, in re-examination for the abnormality, it is possible to display a guide to the abnormality. This guide may be displayed as the positional coordinates (X, Y, Z, θx, θy, θz).

In addition, in the open operation, the absolute coordinates of the abnormality are available. If an operator understands such information, a certain visual perception for an operation is possible without a direct marking on the subject and so on.

Furthermore, this information is effective for a biopsy operation. It is popular that a biopsy guide is displayed on a real-time ultrasonic image when performing a biopsy operation. The biopsy guide indicates a route for biopsy needle to be inserted to an affected region. In this case, the information mentioned above is used for calculating the biopsy guide. Accordingly, accuracy and efficiency of the examination are both improved.

(Fifth Exemplary Embodiment)

In the above mentioned exemplary embodiment, the position sensor 60 of ultrasonic probe is based on a magnetic field. Such a magnetic sensor has enough accuracy in an ideal environment. However, in an environment where an ultrasonic diagnostic apparatus is usually used, there may be things which disturb a magnetic field, such as a bed made from steel. In this fifth exemplary embodiment, an ultrasonic diagnostic apparatus has a means for correcting such disturbance.

In an operation of this exemplary embodiment, at first, an operator measures a disturbance of the magnetic field.

In particular, an operator measures the magnetic field at several points by moving the ultrasonic probe to the left, right, top and bottom. For example, the ultrasonic probe is positioned at a plurality of ends of a bar, board or cube having a size already known and an operator pushes a predetermined button on the ultrasonic probe. This manner enables measurement of the magnetic field at a plurality of points having an already known positional relationship.

By this measurement, the controller acquires strength of the magnetic field recognized by the position sensor 60. At the next step, the controller compares the magnetic field ideally calculated from the position of the ultrasonic probe 10 with magnetic field actually recognized by the position sensor 60.

Figure 18:
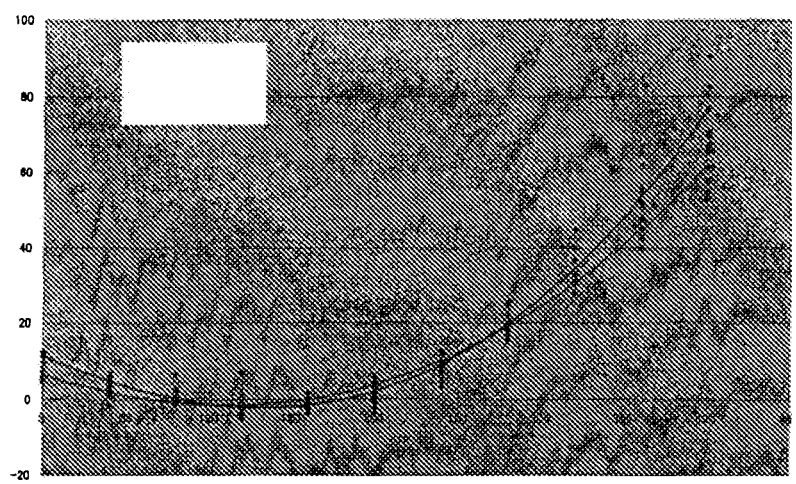
FIG. 18 is an abstract chart for an explanation of correction of a magnetic field of the fifth exemplary embodiment.

FIG. 18 shows a graph indicating a relationship between magnetic field ideally calculated and magnetic field actually recognized by the position sensor 60. As shown in FIG. 18, the magnetic field can be fitted to a quadratic curve or a cubic curve and so on. The controller memorizes such a relationship and calculates correct positional information by inverse transform of measured space.

(Sixth Exemplary Embodiment)

Figure 19:
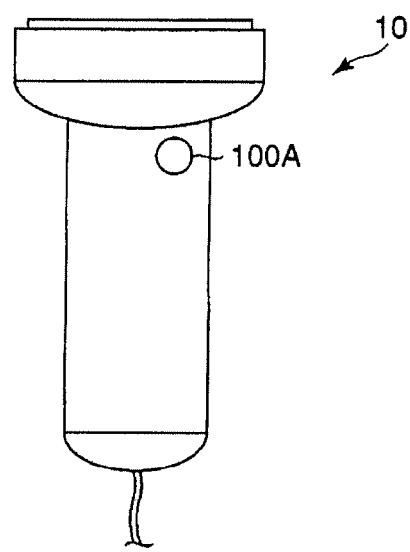
FIG. 19 is an abstract chart of an ultrasonic probe of a sixth exemplary embodiment.

Next, a sixth exemplary embodiment is explained with reference to FIG. 19.

In the above mentioned exemplary embodiment, as soon as the touch detection unit 100 detects a contact with the subject S. Memorizing of a positional coordinates and generating of the probe mark PM, the locus mark LM and scan plane mark SM are started. However, in this exemplary embodiment, as shown in FIG. 19, manual push switch 100A is used as a trigger for generating the probe mark PM, the locus mark LM and scan plane mark SM instead of touch detection unit 100.

The push switch 100A is fixed on the ultrasonic probe 10, and can easily be operated by an operator grabbing the ultrasonic probe 10. When the push switch 100A is turned on, memorizing of positional coordinates commences. When the push switch 100A is turned off, a memorizing of a positional coordinates ceases.

Compared to the first exemplary embodiment, a turning operation of an operator is necessary for this exemplary embodiment. However, by a very simple system, generating of the probe mark PM, the locus mark LM and scan plane mark SM is started. Furthermore, because of fixing the push switch 100A on the ultrasonic probe 10, the turning operation is very easy.

(Seventh Exemplary Embodiment)

Figure 20:
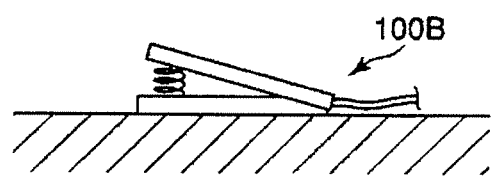
FIG. 20 is an abstract chart of a foot switch of a seventh exemplary embodiment.

Next, a seventh exemplary embodiment is explained with reference to FIG. 20.

In the above mentioned exemplary embodiment, as soon as the touch detection unit 100 detects a contact with the subject S, memorizing of a positional coordinates and generating of the probe mark PM, the locus mark LM and scan plane mark SM commences. However, in this exemplary embodiment, as shown in FIG. 20, a foot switch operated by a foot 100B is used as a trigger for generating of the probe mark PM, the locus mark LM and scan plane mark SM, instead of touch detection unit 100.

The foot switch 100B is laid on a floor and an operator can easily turn it on/off. When the operator's foot turns on the foot switch 100B, memorizing of a positional coordinates is started. When the foot switch 100B is turned off, memorizing of a positional coordinates is stopped.

In this exemplary embodiment, the operator has a free hand other than the hand having the ultrasonic probe, even at the time of turning on/off the switch. Thus, accuracy and efficiency of examination are improved.

(Eighth Exemplary Embodiment)

Figure 21:
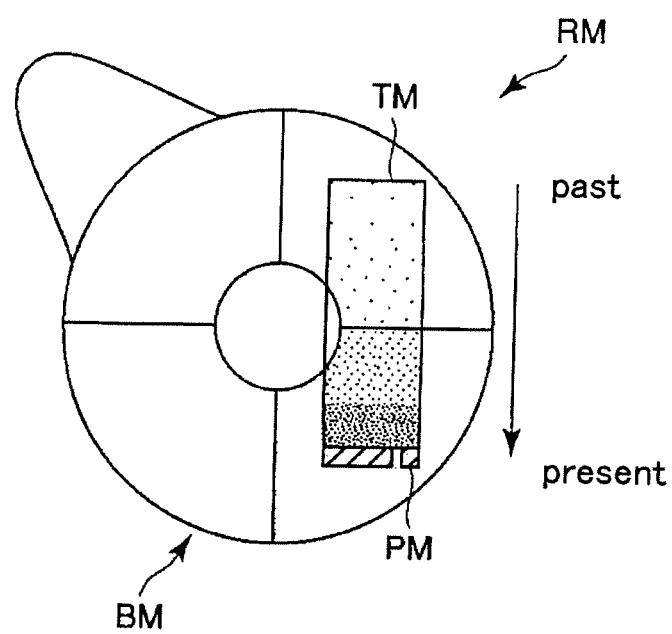
FIG. 21 is an abstract chart of the reference mark indicating the time in the eighth exemplary embodiment.
Figure 22:
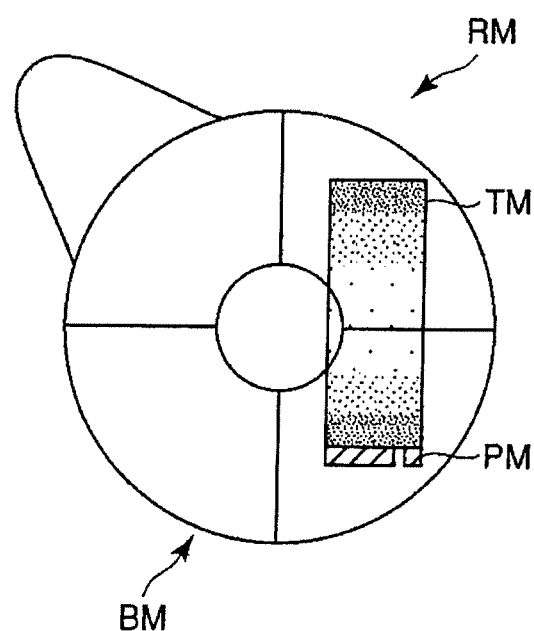
FIG. 22 is an abstract chart of the reference mark indicating the moving speed of the ultrasonic probe of the eighth exemplary embodiment.

Next, an eighth exemplary embodiment is explained with reference to FIG. 21.

As shown in FIG. 13, on a reference mark RM of this exemplary embodiment, a color of the locus mark becomes deeper as time goes by from initial contact of ultrasonic probe with the subject S. Therefore, an operator can understand a start point and finish point of a movement of the ultrasonic probe 10 by watching a shading of color of the locus mark.

In addition, as shown in FIG. 14, a shading of color of the locus mark may be changed according to a speed of movement of ultrasonic probe. In this manner, an operator can move the ultrasonic probe 10 at a suitable speed. Thus, too fast speed of moving of the ultrasonic probe 10 leading to overlooking an abnormality and too slow speed of moving of the ultrasonic probe 10 leading to prolonged examination are reduced. Furthermore a color itself of the locus mark may be changed according to a speed or period of movement of the ultrasonic probe.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

The invention claimed is:

1. An ultrasonic diagnostic apparatus, comprising:
   an ultrasonic probe configured to transmit and receive ultrasonic waves toward a part of a subject during scanning movement of the ultrasonic probe across an external body surface of the subject;
   processing circuitry configured to detect time-series positions of the ultrasonic probe which contacts the external body surface while scanning the part of the subject;
   a locus region generator configured to generate a locus region two-dimensionally representing a region scanned by the ultrasonic probe within a predetermined entire region represented as a body mark;
   a memory to store the locus region; and
   a controller configured to cause a display to display a surface map that includes the locus region stored in the memory.

2. The ultrasonic diagnostic apparatus according to claim 1, further comprising:
   a mark generator configured to generate the body mark indicating the part of the subject; and
   a display processor configured to display the ultrasonic image and the body mark, wherein
   the controller controls the display processor to display the locus region, superimposed on the body mark.

3. The ultrasonic diagnostic apparatus according to claim 2, wherein:
   the mark generator is configured to generate a probe mark indicating a position of the ultrasonic probe according to the time-series positions detected by the processing circuitry; and
   the display processor is configured to display the probe mark superimposed on the body mark.

4. The ultrasonic diagnostic apparatus according to claim 1, further comprising an image sensor configured to detect a direction and displacement of the ultrasonic probe.

5. The ultrasonic diagnostic apparatus according to claim 1, wherein the controller is configured to start generation of the locus region when contact of the ultrasonic probe with the body surface of the subject is detected.

6. The ultrasonic diagnostic apparatus according to claim 2, further comprising:
   a manual switch provided on the ultrasonic probe,
   wherein the controller is configured to start generation of the locus region according to operating of the manual switch.

7. The ultrasonic diagnostic apparatus according to claim 1, further comprising:
   a foot switch configured to be operated by a foot of the operator,
   wherein the controller is configured to start generation of the locus region according to operating of the foot switch.

8. The ultrasonic diagnostic apparatus according to claim 2, wherein:
   the controller causes the display processor to display the locus region indicating a time passage from start time of generation of the locus region by a change of color tone or shading.

9. The ultrasonic diagnostic apparatus according to claim 2, wherein:
   the controller causes the display processor to display the locus region, indicating moving speed of the probe by a change of color tone or shading.

10. The ultrasonic diagnostic apparatus according to claim 2, wherein:
    the mark generator is configured to generate a scan plane mark indicating imaged region at a present time, wherein
    the display processor is configured to display the scan plane mark with the probe mark.

11. The ultrasonic diagnostic apparatus according to claim 10, wherein:
    the mark generator is configured to generate the scan plane mark according to a depth of the ultrasonic image set in the signal processor.

12. The ultrasonic diagnostic apparatus according to claim 10, wherein:
the mark generator is configured to generate the scan plane mark according to an aperture of a scanned range set in the signal processor.

13. The ultrasonic diagnostic apparatus according to claim 10, wherein:
the mark generator is configured to generate the scan plane mark according to what kind of the ultrasonic probe is being used.

14. The ultrasonic diagnostic apparatus according to claim 1, wherein:
the mark generator is configured to generate a lattice pattern, a scaled axis or a dots pattern to be superimposed on the body mark.

15. The ultrasonic diagnostic apparatus according to claim 2, wherein:
the mark generator is configured to generate a three dimensional body mark for indicating a three dimensional form of the subject; and
the controller is configured to indicate a three dimensional locus by changing at least one of brightness, color and transparency of a region of the subject already imaged.

16. The ultrasonic diagnostic apparatus according to claim 1, further comprising:
an operation panel configured so that the operator can assign a point to the ultrasonic image, wherein
the controller is further configured to control the memory to store positional coordinates of the point assigned by the operation panel on the basis of the position detected by the processing circuitry; and
the display is further configured to indicate the positional coordinates.

* * * * *